United States Patent [19]

Connor et al.

[11] Patent Number: 5,760,050
[45] Date of Patent: Jun. 2, 1998

[54] ANTIPSYCHOTIC METHOD UTILIZING CERTAIN TETRAHYDROCHROMENO[3,4-C] PYRIDIN-5-ONES

[75] Inventors: David Thomas Connor; Steven Robert Miller; Paul Charles Unangst; Lawrence David Wise, all of Ann Arbor, Mich.

[73] Assignee: Warner-Lambert Company, Morris Plains, N.J.

[21] Appl. No.: 807,517

[22] Filed: Feb. 27, 1997

Related U.S. Application Data

[60] Provisional application No. 60/013,011 Mar. 7, 1996.
[51] Int. Cl.$^6$ .............. A61K 31/44; C07D 491/052
[52] U.S. Cl. .............. 514/291; 546/89; 546/92
[58] Field of Search .............. 546/89, 92; 514/291

[56] References Cited

U.S. PATENT DOCUMENTS

| | | | |
|---|---|---|---|
| 3,396,165 | 8/1968 | Bolger et al. | 260/247.2 |
| 3,396,166 | 8/1968 | Bolger et al. | 260/247.2 |
| 3,514,464 | 5/1970 | Pars et al. | 260/295 |
| 3,635,993 | 1/1972 | Pars et al. | 260/297 |
| 3,962,266 | 6/1976 | Brown | 546/92 |
| 4,382,939 | 5/1983 | Connor et al. | 260/297 |
| 5,633,376 | 5/1997 | Thurkauf | 544/360 |

OTHER PUBLICATIONS

Rowley M et al. J. Med. Chem. 39, 1943–1945, 1996.
Kulagowski JJ et al. J. Med. Chem. 39, 1941–1942, 1996.
Connor et al., *J. Heterocyclic Chem.*, vol. 21, 1984, pp. 1557–1559.
Joshi et al., *Indian Journal of Chemistry*, vol. 19B, 1980, pp. 495–499.

*Primary Examiner*—Evelyn Huang
*Attorney, Agent, or Firm*—Charles W. Ashbrook; Michael J. Atkins

[57] ABSTRACT

1,2,3,4-Tetrahydro-chromeno[3,4-c]pyridin-5-ones of the formula

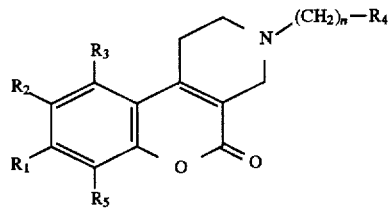

wherein $R_1$, $R_2$, $R_3$, and $R_5$ include hydrogen, alkyl, alkoxy, hydroxy, halo, nitro, amino, and trifluoromethyl; $R_4$ is unsubstituted or substituted phenyl, pyridyl, or quinolinyl; and n is 0 to 4, are useful to treat psychosis in mammals, particularly schizophrenia.

16 Claims, No Drawings

ANTIPSYCHOTIC METHOD UTILIZING CERTAIN TETRAHYDROCHROMENO[3,4-C] PYRIDIN-5-ONES

FIELD OF THE INVENTION

This application claims the benefit of U.S. Provisional application Ser. No. 60/013,011 filed Mar. 7, 1996.

This invention provides a method for treating psychosis utilizing 1,2,3,4-tetrahydro-chromeno[3,4-c]-pyridin-5-ones.

BACKGROUND OF THE INVENTION

Compounds which antagonize dopamine receptors are useful as antipsychotic agents. Several individual and distinct dopamine receptors have been identified, including the $D_2$, $D_3$, and $D_4$ receptors. Antagonism of the $D_2$ receptor has been associated with undesirable biological effects, for example extrapyramidal side effects and tardive dyskinesia, as well as desirable efficacy. In contrast, compounds that selectively antagonize the $D_4$ receptor have been shown to exhibit good efficacy in psychotic disorders such as schizophrenia with minimal side effects. For example, the antipsychotic agent clozapine has a 10-fold higher affinity for the dopamine $D_4$ receptor than for the $D_2$ receptor, and improves both the positive and negative symptoms of schizophrenia with low incidence of extrapyramidal side effects.

We have now discovered a series of 1,2,3,4-tetrahydrochromeno[3,4-c]pyridin-5-ones which are selective dopamine $D_4$ antagonists, and as such are useful to treat psychotic conditions such as schizophrenia.

SUMMARY OF THE INVENTION

This invention provides a method for treating psychosis in mammals in need of treatment by administering an effective amount of a 1,2,3,4-tetrahydro-chromeno[3,4-c]pyridin-5-one. The method more particularly comprises administering a compound defined by Formula I

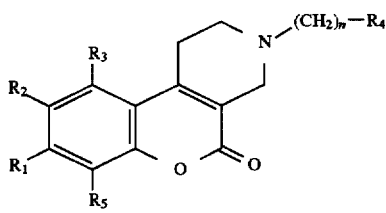

wherein:

$R_1$ is hydrogen, hydroxy, lower alkyl, or lower alkoxy;

$R_2$, $R_3$, and $R_5$ independently are hydrogen, hydroxy, lower alkyl, lower alkoxy, halo, nitro, amino, or trifluoromethyl;

$R_4$ is phenyl, substituted phenyl, pyridyl, substituted pyridyl, quinolinyl, or substituted quinolinyl;

n is 0, 1, 2, 3, or 4;

and the pharmaceutically acceptable salts thereof.

In a preferred embodiment, the antipsychotic method utilizes a compound of Formula I wherein n is 1, and $R_4$ is phenyl or phenyl substituted with one, two, or three groups selected from lower alkyl, lower alkoxy, hydroxy, trifluoromethyl, halo, and nitro. An additionally preferred method employs compounds of Formula I wherein $R_4$ is pyridyl or quinolinyl.

Another preferred method employs compounds of Formula I wherein $R_1$ is hydroxy or methoxy, $R_2$ is hydrogen, hydroxy, or methoxy, and $R_3$ and $R_5$ both are hydrogen. The most preferred method employs the foregoing compounds wherein n is 1, and $R_4$ is phenyl or phenyl substituted with chloro, methyl, methoxy, or trifluoromethyl.

Another embodiment of the invention are compounds selected from:

3-Benzyl-8-methoxy-1,2,3,4-tetrahydro-chromeno[3,4-c]pyridin-5-one;

8-Methoxy-3-(4-methyl-benzyl)-1,2,3,4-tetrahydrochromeno[3,4-c]pyridin-5-one;

3-(3,4-Dichloro-benzyl)-8-methoxy-1,2,3,4-tetrahydrochromeno[3,4-c]pyridin-5-one;

8-Methoxy-3-(4-nitro-benzyl)-1,2,3,4-tetrahydro-chromeno[3,4-c]pyridin-5-one;

3-Benzyl-8,9-dimethoxy-1,2,3,4-tetrahydro-chromeno[3,4-c]pyridin-5-one;

3-Benzyl-9-hydroxy-8-methyl-1,2,3,4-tetrahydro-chromeno[3,4-c]pyridin-5-one hydrochloride;

3-Benzyl-8,10-dihydroxy-9-methyl-1,2,3,4-tetrahydrochromeno[3,4-c]pyridin-5-one hydrochloride;

3-(4-Chloro-benzyl)-8-methoxy-1,2,3,4-tetrahydrochromeno[3,4-c]pyridin-5-one;

8-Methoxy-3-pyridin-4-ylmethyl-1,2,3,4-tetrahydrochromeno[3,4-c]pyridin-5-one;

8-Methoxy-3-quinolin-4-ylmethyl-1,2,3,4-tetrahydrochromeno[3,4-c]pyridin-5-one;

8-Methoxy-3-(3,4,5-trimethoxy-benzyl)-1,2,3,4-tetrahydrochromeno[3,4-c]pyridin-5-one;

8-Methoxy-3-(4-trifluoromethyl-benzyl)-1,2,3,4-tetrahydro-chromeno[3,4-c]pyridin-5-one;

8-Methoxy-3-(4-methoxy-benzyl)-1,2,3,4-tetrahydrochromeno[3,4-c]pyridin-5-one;

3-(3-Chloro-benzyl)-8-methoxy-1,2,3,4-tetrahydrochromeno[3,4-c]pyridin-5-one;

3-(2-Chloro-benzyl)-8-methoxy-1,2,3,4-tetrahydrochromeno[3,4-c]pyridin-5-one;

3-Benzyl-8-methyl-1,2,3,4-tetrahydro-chromeno[3,4-c]pyridin-5-one;

8-Methoxy-3-pyridin-3-ylmethyl-1,2,3,4-tetrahydrochromeno[3,4-c]pyridin-5-one;

8-Methoxy-3-pyridin-2-ylmethyl-1,2,3,4-tetrahydrochromeno[3,4-c]pyridin-5-one;

3-(4-Chloro-benzyl)-8-methyl-1,2,3,4-tetrahydro-chromeno [3,4-c]pyridin-5-one;

3-(4-Chloro-benzyl)-8,9-dimethoxy-1,2,3,4-tetrahydrochromeno[3,4-c]pyridin-5-one;

8-Methoxy-3-phenethyl-1,2,3,4-tetrahydro-chromeno[3,4-c]pyridin-5-one;

3-Benzyl-7,8-dimethoxy-1,2,3,4-tetrahydro-chromeno[3,4-c]pyridin-5-one; and 8,9-Dimethoxy-3-phenethyl-1,2,3,4-tetrahydro-chromeno [3,4-c]pyridin-5-one hydrochloride.

Still another embodiment are pharmaceutical formulations comprising the foregoing specific compounds together with a diluent, carrier, or excipient therefor.

DETAILED DESCRIPTION OF THE INVENTION

In the above Formula I defining the compounds to be employed in the present method, $R_1$ includes lower alkyl and lower alkoxy. The term "lower alkyl" means a straight or branched carbon chain having from 1 to 6 carbon atoms, examples of which include methyl, ethyl, isopropyl, tert.-butyl, 1,1-dimethylbutyl, n-pentyl, isohexyl, and the like. "Lower alkoxy" means the foregoing lower alkyl groups linked through an oxygen atom. Examples of lower alkoxy groups include methoxy, ethoxy, isopropoxy, isobutoxy, n-pentoxy, n-hexyloxy, and the like. $R_2$, $R_3$, and $R_5$ can be lower alkyl and lower alkoxy, as well as halo such as fluoro, chloro, bromo, and iodo.

R₄ in the above Formula I is phenyl, pyridyl or quinolinyl, and substituted phenyl, substituted pyridyl, and substituted quinolinyl. Typical substituent groups include lower alkyl and lower alkoxy, as those groups are defined above. Other substituents include halo, which means bromo, chloro, fluoro, and iodo. Typical substituted phenyl groups thus include 2-fluorophenyl, 3-bromophenyl, 4-ethoxyphenyl, 2-nitrophenyl, 3-chloro-5-hydroxyphenyl, 4-tert.-butylphenyl, 2,6-diethyl-4-trifluoromethylphenyl, and the like. The pyridyl and quinolinyl groups can be similarly substituted, for example 2-chloro-4-pyridyl, 2,5-dimethyl-3-pyridyl, 4-trifluoromethyl-5-nitro-2-pyridyl, 5-chloro-4-quinolinyl, 6,7-dimethoxy-4-quinolinyl, 8-nitro-2-quinolinyl, 2-isopropoxy-7-iodo-4-quinolinyl, and the like.

The compounds to be employed in the antipsychotic method of this invention can be prepared from readily available starting materials utilizing general synthetic techniques known to those skilled in the art of organic chemistry. For example, a phenol or substituted phenol readily reacts with an unsubstituted or N-substituted 3-alkoxycarbonyl-4-oxo-piperidine in the presence of an acid to form a chromeno [3,4-c]-pyridin-5-one of Formula I. The reaction is illustrated in the following scheme:

Certain N-substituent groups such as benzyl, 4-nitrobenzyl, and the like, are readily converted to N-unsubstituted derivatives by normal hydrogenolysis, for example by reaction with hydrogen in the presence of a catalyst such as palladium on carbon, generally in a solvent such as tetrahydrofuran, dioxane, methanol, or the like.

The N-unsubstituted chromeno pyridines are readily alkylated by reaction with an aryl alkyl halide to give the corresponding N-substituted chromeno pyridine according to the following scheme:

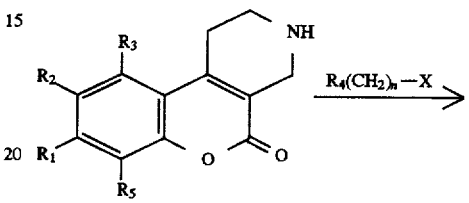

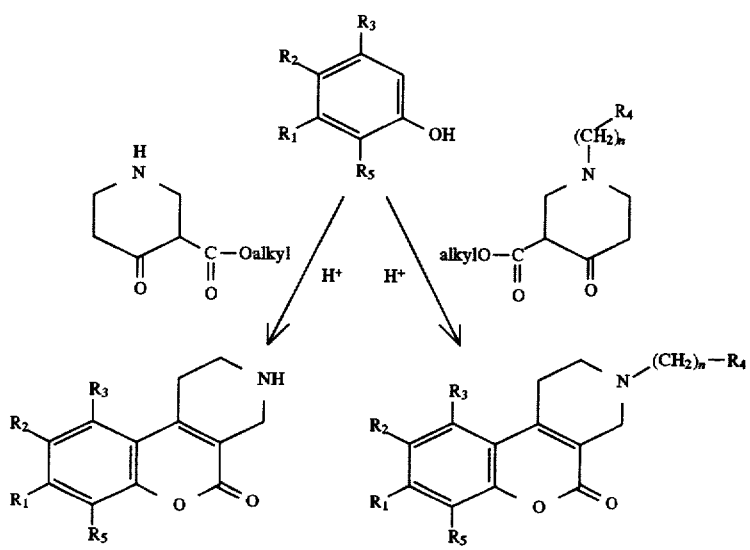

R₁, R₂, R₃, R₄, R₅, and n in the foregoing structures are as defined above, and alkyl is lower alkyl such as methyl, ethyl, tert.-butyl, and the like. The reaction between the phenol and the piperidine generally is carried out by mixing approximately equimolar quantities of the reactants in a mutual solvent such as water, dioxane, or the like, in the presence of a protonic acid such as hydrochloric acid, sulfuric acid, phosphoric acid, or the like. The reaction typically is complete after about 24 to about 48 hours when carried out at a temperature of about 0° C. to about 50° C., typically at about 25° C. The product chromeno pyridine compound typically is isolated by making the reaction mixture alkaline to pH of about 10 to about 11, for example, by adding a base such as aqueous sodium hydroxide or ammonium hydroxide. The product typically precipitates and can be recovered by filtration. Further purification can be accomplished by crystallization from common organic solvents such as methanol, isopropanol, and the like.

-continued

where R₁, R₂, R₃, R₄, R₅, and n are as defined above, and X is a leaving group such as chloro, bromo, iodo, p-toluenesulfonyl, and the like. The reaction is carried out by mixing approximately equimolar quantities of the alkylating agent and chromeno pyridine in a mutual solvent such as dimethylformamide, dimethylsulfoxide, or the like, preferably in the presence of an equimolar quantity of a base such as sodium carbonate, potassium carbonate, or the like. The reaction is normally complete within 2 to 8 hours when carried out at a temperature of about 40° C. to about 100° C. The product can be isolated by removing the reaction solvent, for example by evaporation under reduced pressure, and extracting the residue into an organic solvent such as ethyl acetate, methylene chloride, or the like. Normal purification procedures such as crystallization from solvents such as methanol, and column chromatography over solid supports such as silica gel, can be utilized as desired.

An alternative method for preparing the N-alkyl chromeno pyridines of Formula I, wherein n is 1, comprises reacting an N-unsubstituted chromeno pyridine with an aldehyde of the formula R₄CHO, in the presence of a reducing agent such as triacetoxyborohydride. The reaction is depicted by the following scheme:

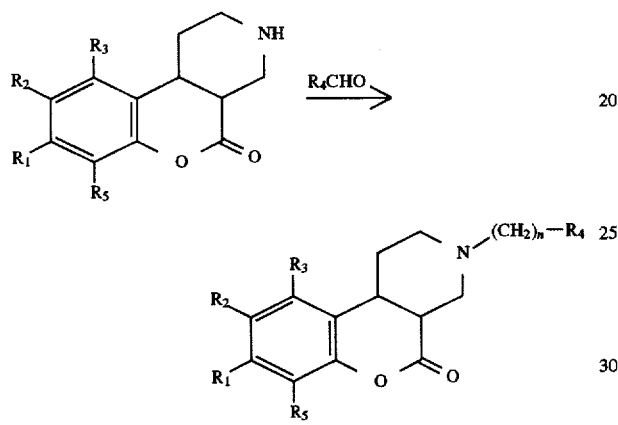

The aldehyde, for example a substituted benzaldehyde, a parietal aldehyde or a quinolinyl aldehyde, is typically mixed with an equimolar quantity of the N-unsubstituted chromeno pyridine in a mutual solvent such as tetrahydrofuran, 1,2-dichloroethane, 1,3-dimethyl-2-imidazolidinone, or the like, and an acid such as acetic acid or the like. The mixture is stirred at about 25° C. for about 10 to about 30 minutes, and a reducing agent such as a borohydride is added. The reaction generally is complete after about 2 to 20 hours, and the product can be isolated by diluting the reaction mixture with water and extracting the product into a water immiscible solvent such as ethyl acetate or the like. Removal of the organic solvent, for instance by evaporation under reduced pressure, provides the desired product, which can be further purified, if desired, by crystallization from common solvents such as ethyl acetate, methanol, and the like.

The synthesis of typical 1,2,3,4-tetrahydro-chromeno[3,4-c]pyridin-5-ones to be employed in the antipsychotic method of this invention is illustrated in the following detailed examples.

EXAMPLE 1

3-Benzyl-8-methoxy-1,2,3,4-tetrahydro-chromeno[3,4-c]-pyridin-5-one

A mixture of 3-methoxyphenol (28.3 g, 227 mmol) and methyl 1-benzyl-4-oxo-3-piperidinecarboxylate hydrochloride (46.1 g, 162 mmol) is cooled in ice and treated dropwise with a solution prepared from 38 mL of water diluted to 150 mL with concentrated sulfuric acid. The mixture is stirred at room temperature for 48 hours, then added slowly to 500 g of ice and 100 mL of concentrated ammonium hydroxide. Additional ice and ammonium hydroxide are added until the pH of the mixture is 10 to 11. Stirring is continued until the initially gummy precipitate becomes granular. The solid is filtered, then stirred in 400 mL of 2.5% aqueous sodium hydroxide solution followed by 400 mL of 10% methanol in water. The solid is again filtered and recrystallized from 2-propanol to yield 24.5 g (47%) of final product; mp 118°–120° C.

EXAMPLE 2

8-Methoxy-1,2,3,4-tetrahydro-chromeno[3,4-c] pyridin-5-one

A solution of 3-benzyl-8-methoxy-1,2,3,4-tetrahydro-chromeno[3,4-c]pyridin-5-one (8.2 g, 26 mmol) in 150 mL of methanol and 100 mL of tetrahydrofuran is hydrogenated at room temperature over a palladium on carbon catalyst (0.85 g) for 18 hours. The catalyst is filtered and the filtrate evaporated. Recrystallization of the residue from acetonitrile with a small amount of added water gives 2.9 g (49%) of product; mp 179°–181° C.

EXAMPLE 3

8-Methoxy-3-(4-methyl-benzyl)-1,2,3,4-tetrahydro-chromeno[3,4-c]pyridin-5-one

A solution of 8-methoxy-1,2,3,4-tetrahydro-chromeno[3,4-c]pyridin-5-one (1.2 g, 5.2 mmol) and 4-methylbenzaldehyde (0.68 g, 5.7 mmol) in 20 mL of tetrahydrofuran and 7 mL of 1,3-dimethyl-2-imidazolidinone is treated with glacial acetic acid (0.29 mL, 5.2 mmol). The mixture is stirred for 10 minutes, and then sodium triacetoxyborohydride (1.6 g, 7.5 mmol) is added in portions over 30 minutes. The mixture is stirred for 16 hours, then added to 300 mL of ice water. The precipitated solid is filtered, washed with water, and recrystallized from ethyl acetate to yield 1.2 g (70%) of product, mp 147°–149° C.

EXAMPLE 4

3-(3,4-Dichloro-benzyl)-8-methoxy-1,2,3,4-tetrahydro-chromeno[3,4-c]pyridin-5-one Prepared by the procedure of Example 3 from 8-methoxy-1,2,3,4-tetrahydro-chromeno[3,4-c]pyridin-5-one and 3,4-dichlorobenzaldehyde. Yield 65%, mp 144°–146° C.

EXAMPLE 5

8-Methoxy-3-(4-nitro-benzyl)-1,2,3,4-tetrahydro-chromeno[3,4-c]pyridin-5-one

A mixture of 8-methoxy-1,2,3,4-tetrahydro-chromeno[3,4-c]pyridin-5-one (1.2 g, 5.2 mmol), potassium carbonate (0.69 g, 5.0 mmol), and 4-nitrobenzyl bromide (1.1 g, 5.1 mmol) in 15 mL of N,N-dimethylformamide is heated at 90° C. for 4 hours. The cooled reaction mixture is evaporated, and the residue partitioned between ethyl acetate and brine. The organic layer is dried (anhydrous magnesium sulfate) and evaporated. Recrystallization of the residue from ethyl acetate gives 0.87 g (47%) of product; mp 176°–178° C.

EXAMPLE 6

3-Benzyl-8,9-dimethoxy-1,2,3,4-tetrahydro-chromeno[3,4-c]pyridin-5-one

Prepared by the procedure of Example 1 from 3,4-dimethoxyphenol and ethyl 1-benzyl-4-oxo-3-piperidinecarboxylate hydrochloride. Yield 40%; mp 189°–191° C.

EXAMPLE 7

3-Benzyl-9-hydroxy-8-methyl-1,2,3,4-tetrahydro-chromeno[3,4-c]pyridin-5-one hydrochloride Prepared by the procedure of Example 1 from 3-methyl-4-hydroxyphenol and ethyl 1-benzyl-4-oxo-3-piperidinecarboxylate hydrochloride. The crude product was converted to the hydrochloride salt. Yield 28%; mp 283°–289° C.

EXAMPLE 8

3-Benzyl-8,10-dihydroxy-9-methyl-1,2,3,4-tetrahydro-chromeno[3,4-c]pyridin-5-one hydrochloride Prepared by the procedure of Example 1 from 3,5-dihydroxy-4-methylphenol and ethyl 1-benzyl-4-oxo-3-piperidinecarboxylate hydrochloride. The crude product was converted to the hydrochloride salt. Yield 24%; mp 293°–299° C.

EXAMPLE 9

3-(4-Chloro-benzyl)-8-methoxy-1,2,3,4-tetrahydro-chromeno[3,4-c]pyridin-5-one

Prepared by the procedure of Example 3 from 8-methoxy-1,2,3,4-tetrahydro-chromeno[3,4-c]pyridin-5-one and 4-chlorobenzaldehyde. Yield 70%; mp 140°–142° C.

EXAMPLE 10

8-Methoxy-3-pyridin-4-ylmethyl-1,2,3,4-tetrahydro-chromeno[3 4-c]pyridin-5-one

Prepared by the procedure of Example 3 from 8-methoxy-1,2,3,4-tetrahydro-chromeno[3,4-c]pyridin-5-one and 4-pyridinecarboxaldehyde. Yield 53%; mp 119°–122° C.

EXAMPLE 11

8-Methoxy-3-quinolin-4-ylmethyl-1,2,3,4-tetrahydro-chromeno[3,4-c]pyridin-5-one

A mixture of 8-methoxy-1,2,3,4-tetrahydro-chromeno[3,4-c]pyridin-5-one (1.0 g, 4.3 mmol), 4-quinolinecarboxaldehyde (0.68 g, 4.3 mmol), and glacial acetic acid (1.75 mL, 30.6 mmol) in 20 mL of 1,2-dichloroethane is treated in small portions with sodium triacetoxyborohydride (1.3 g, 6.1 mmol). The mixture is stirred at room temperature for 24 hours. Water (100 mL) is slowly added, followed by concentrated ammonium hydroxide until slight basicity. The mixture is extracted with dichloromethane, and the combined organic layers are washed with brine, dried (anhydrous sodium sulfate), and evaporated. Purification of the residue by flash chromatography (silica gel, 3% methanol in dichloromethane elution) gives 0.70 g (42%) of product; mp 186°–188° C.

EXAMPLE 12

8-Methoxy-3-(3,4,5-trimethoxy-benzyl)-1,2,3,4-tetrahydro-chromeno[3,4-c]pyridin-5-one Prepared by the procedure of Example 3 from 8-methoxy-1,2,3,4-tetrahydro-chromeno[3,4-c]pyridin-5-one and 3,4,5-trimethoxybenzaldehyde. Yield 72%; mp 171°–173° C.

EXAMPLE 13

8-Methoxy-3-(4-trifluoromethyl-benzyl)-1,2,3,4-tetrahydro-chromeno[3,4-c]pyridin-5-one Prepared by the procedure of Example 3 from 8-methoxy-1,2,3,4-tetrahydro-chromeno[3,4-c]pyridin-5-one and 4-trifluoromethylbenzaldehyde. Yield 70%; mp 203°–206° C.

EXAMPLE 14

8-Methoxy-3-(4-methoxy-benzyl)-1,2,3,4-tetrahydro-chromeno[3,4-c]pyridin-5-one

Prepared by the procedure of Example 3 from 8-methoxy-1,2,3,4-tetrahydro-chromeno[3,4-c]pyridin-5-one and 4-methoxybenzaldehyde. Yield 54%; mp 101°–103° C.

EXAMPLE 15

3-(3-Chloro-benzyl)-8-methoxy-1,2,3,4-tetrahydro-chromeno[3,4-c]pyridin-5-one

Prepared by the procedure of Example 3 from 8-methoxy-1,2,3,4-tetrahydro-chromeno[3,4-c]pyridin-5-one and 3-chlorobenzaldehyde. Yield 65%; mp 112°–115° C.

EXAMPLE 16

3-(2-Chloro-benzyl)-8-methoxy-1,2,3,4-tetrahydro-chromeno[3,4-c]pyridin-5-one

Prepared by the procedure of Example 3 from 8-methoxy-1,2,3,4-tetrahydro-chromeno[3,4-c]pyridin-5-one and 2-chlorobenzaldehyde. Yield 65%; mp 137°–139° C.

EXAMPLE 17

3-Benzyl-8-methyl-1,2,3,4-tetrahydro-chromeno[3,4-c]pyridin-5-one

Prepared by the procedure of Example 1 from 3-methylphenol and ethyl 1-benzyl-4-oxo-3-piperidinecarboxylate hydrochloride. Yield 60%; mp 109°–111° C.

EXAMPLE 18

8-Methoxy-3-pyridin-3-ylmethyl-1,2,3,4-tetrahydro-chromeno[3,4-c]pyridin-5-one

Prepared by the procedure of Example 3 from 8-methoxy-1,2,3,4-tetrahydro-chromeno[3,4-c]pyridin-5-one and 3-pyridinecarboxaldehyde. Yield 19%; mp 107°–110° C.

EXAMPLE 19

8-Methoxy-3-pyridin-2-ylmethyl-1,2,3,4-tetrahydro-chromeno[3,4-c]pyridin-5-one

Prepared by the procedure of Example 3 from 8-methoxy-1,2,3,4-tetrahydro-chromeno[3,4-c]pyridin-5-one and 2-pyridinecarboxaldehyde. Yield 25%; mp 140°–142° C.

EXAMPLE 20

3-(4-Chloro-benzyl)-8-methyl-1,2,3,4-tetrahydro-chromeno[3,4-c]pyridin-5-one

Prepared by the procedure of Example 3 from 8-methyl-1,2,3,4-tetrahydro-chromeno[3,4-c]pyridin-5-one* and 4-chlorobenzaldehyde. Yield 65%; mp 147°–149° C.

EXAMPLE 21

3-(4-Chloro-benzyl)-8,9-dimethoxy-1,2,3,4-tetrahydro-chromeno[3,4-c]pyridin-5-one Prepared by the procedure of Example 3 from 8,9-dimethoxy-1,2,3,4-tetrahydro-chromeno[3,4-c]-pyridin-5-one* and 4-chlorobenzaldehyde. Yield 48%; mp 173°–175° C.

*Connor D. T., Schwender C. F., Sorenson R. J., and Unangst P. C., U.S. Pat. No. 4,382,939 (May 10, 1983).

EXAMPLE 22

8-Methoxy-3-phenethyl-1,2,3,4-tetrahydro-chromeno[3,4-c]pyridin-5-one

A mixture of 8-methoxy-1,2,3,4-tetrahydro-chromeno[3,4-c]pyridin-5-one (1.5 g, 6.5 mmol), potassium carbonate (0.50 g, 4.7 mmol), and (2-bromethyl)benzene (1.0 mL, 1.4 g, 7.3 mmol) in 10 mL of N,N-dimethylformamide is heated at 900 for 18 hours. The cooled reaction mixture is added to 300 mL of water and 150 mL of ethyl ether. The insoluble material is filtered and washed with fresh ethyl ether. Recrystallization of the solid from aqueous 2-propanol gives 0.60 g (27%) of product; mp 135°–136° C.

EXAMPLE 23

8,9-Dimethoxy-3-phenethyl-1,2,3 4-tetrahydro-chromeno[3,4-c]pyridin-5-one hydrochloride A mixture of 8,9-dimethoxy-1,2,3,4-tetrahydro-chromeno[3,4-c]pyridin-5-one (5.2 g, 20 mmol), (2-bromoethyl)benzene (3.0 mL, 4.1 g, 22 mmol), and triethylamine (2.9 mL, 2.1 g, 21 mmol), in 600 mL of ethanol is heated at reflux for 16 hours. The warm reaction mixture is treated with excess hydrogen chloride gas. The mixture is cooled and the precipitated solid filtered and recrystallized from water to yield 3.3 g (39%) of product; mp 220°–223° C.

EXAMPLE 24

3-Benzyl-7,8-dimethoxy-1,2,3,4-tetrahydro-chromeno[3,4-c]pyridin-5-one

Prepared by the procedure of Example 1 from 2,3-dimethoxyphenol and methyl 1-benzyl-4-oxo-3-piperidine-carboxylate hydrochloride. Yield 35%; mp 138°–140° C.

The compounds of Formula I can exist as pharmaceutically acceptable salts, which are prepared by reacting the free tetrahydro pyridine base with an organic or inorganic acid. Typical acids commonly employed include acetic acid, tartaric acid, maleic acid, hydrochloric acid, p-toluenesulfonic acid, sulfuric acid, phosphoric acid, citric acid, and the like. The salts typically are highly crystalline and are readily crystallized from common solvents such as methanol, diethyl ether, chloroform, and the like.

As noted above, the compounds of Formula I are selective dopamine $D_4$ antagonists, and as such are useful for treating psychosis such as schizophrenia. The compounds have been evaluated in standard in vitro assays to determine their ability to bind to specific dopamine receptors.

Compounds of Formula I were tested for their ability to bind to dopamine receptors as measured by their inhibition of [$^3$H]spiperone binding to the human $D_2$ and $D_3$ receptors in an assay described by MacKenzie R. G., VanLeeuwen D., Pugsley T. A., et al., "Characterization of the human dopamine $D_3$ receptor expressed in transfected cell lines." Eur. J. Pharmacol.-Mol. Pharmacol., 1994;266:79–85; for the human $D_4$ dopamine receptor in an assay described by Pugsley T. A., David M. D., Akunne H. C., et al., "CI-1007, a dopamine partial agonist and potential antipsychotic agent. I. Neurochemical Effects." J. Pharmacol. Exp. Ther., 1995;274:898–911; and for ability to block the action of an agonist in a [$^3$H]thymidine incorporation assay described by Lajiness N. E., Chio C. L., Huff R. M., "$D_2$ dopamine receptor stimulation of mitogenesis in transfected Chinese hamster ovary cells: relationship to dopamine stimulation of tyrosine phosphorylations." J. Pharmacol. Exp. Ther., 1993;267:1573–81. This test determines the agonist/antagonist character of a compound by measuring [$^3$H] thymidine uptake in Chinese hamster ovary (CHO) pro-5 cells expressing the dopamine $D_4$ receptor. Agonists, such as quinpirole, promote cell growth and subsequent [$^3$H] thymidine incorporation, while antagonists block the action of agonists. Compounds of Formula I were shown to be antagonists by blocking the action of quinpirole. The above articles are incorporated herein by reference for their assay methodology.

The binding data in the table below shows the selective dopamine antagonist activity of representative compounds of Formula I.

| Example | Dopamine Receptor Binding (Ki, nM) | | |
|---|---|---|---|
| No. | $D_4$ | $D_2$ | $D_3$ |
| 1 | 1.50 | 436 | 60 |
| 3 | 2.6 | 1171 | 491 |
| 4 | 60.9 | — | — |
| 5 | 7.53 | >5882 | >3060 |
| 6 | 59.0 | — | — |
| 7 | 8.01 | 1902 | 295 |
| 8 | 44.3 | — | — |
| 9 | 7.3 | >5882 | 11,727 |
| 10 | 73.5 | — | — |
| 11 | 34.3 | — | — |
| 12 | 21.3 | 2673 | 3667 |
| 13 | 8.18 | 3698 | 966 |
| 14 | 84.3 | — | — |
| 15 | 17.2 | 5504 | 2628 |
| 16 | 33.9 | >5882 | 2612 |
| 17 | 3.59 | 774 | 338 |
| 18 | 21.3 | 3979 | — |
| 19 | 48.0 | — | — |
| 20 | 10.6 | 1166 | — |
| 21 | 8.46 | >5882 | >3030 |
| 22 | 6.87 | >5882 | 591 |
| 23 | 32.6 | — | — |
| 24 | 16.2 | — | — |

For use as antipsychotic agents, the compounds of Formula I will be formulated for convenient administration to humans by any of several routes. The compounds can be administered orally, parenterally, transdermally, rectally, and the like. For oral use, the compounds will be formulated with common excipients such as potato starch, talc, sugar, and the like, and molded or pressed into tablets, or placed into empty gelatin capsules. Binders such as polyvinylpyrrolidone and N-methylcellulose can be employed as desired. Slow-release formulations can be developed by including polymers such as NPV, lactic-glycolic copolymers, and the like.

The compounds can additionally be formulated for parenteral administration, for instance by intramuscular injection or intravenous infusion. The compounds can be dissolved in isotonic saline or 5% aqueous glucose. Common stabilizers and preservatives can be employed, if desired.

The compounds can be formulated for topical administration as creams, salves, lotions, controlled-release patches, and the like. Such formulations will include, for example, gelatins, methylcellulose, dextrin, low melting waxes, cocoa butter, sodium carboxymethyl cellulose, and the like.

The formulations typically will contain from about 1% to about 80% by weight of a compound of Formula I; ideally from about 5% to about 70% by weight, the remainder being one or more of the common excipients, carriers, and adjuvants as mentioned above. The compounds will be administered at a dosage effective to treat the psychotic condition, such as schizophrenia, for example without causing unacceptable side effects. Typical effective amounts will be from about 0.5 to about 250 mg per kilogram of body weight. Such doses can be given from one to about four times a day, or as needed to properly control and treat the psychotic condition.

We claim:

1. A method for treating psychosis in humans in need of treatment comprising administering an effective amount of a compound having the formula

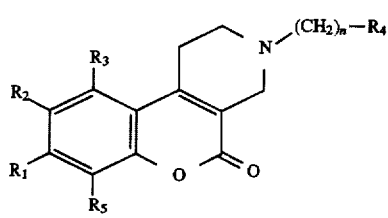

wherein:

$R_1$ is hydrogen, hydroxy, lower alkyl, or lower alkoxy;

$R_2$, $R_3$, and $R_5$ independently are hydrogen, hydroxy, lower alkyl, lower alkoxy, halo, nitro, amino, or trifluoromethyl;

$R_4$ is phenyl, substituted phenyl, pyridyl, substituted pyridyl, quinolinyl, or substituted quinolinyl;

n is 0, 1, 2, 3, or 4;

and the pharmaceutically acceptable salts thereof.

2. A method of claim 1 employing a compound wherein n is 1 and $R_4$ is phenyl.

3. A method of claim 2 employing a compound wherein $R_3$ is hydrogen.

4. A method of claim 3 employing a compound selected from:
3-Benzyl-8-methoxy-1,2,3,4-tetrahydro-chromeno[3,4-c]pyridin-5-one;
3-Benzyl-8,9-dimethoxy-1,2,3,4-tetrahydro-chromeno[3,4-c]pyridin-5-one;
3-Benzyl-9-hydroxy-8-methyl-1,2,3,4-tetrahydro-chromeno[3,4-c]pyridin-5-one hydrochloride; and
3-Benzyl-8-methyl-1,2,3,4-tetrahydro-chromeno[3,4-c]pyridin-5-one.

5. A method of claim 2 employing 3-Benzyl-8,10-dihydroxy-9-methyl-1,2,3,4-tetrahydro-chromeno[3,4-c]pyridin-5-one.

6. A method of claim 1 employing a compound wherein n is 1, and $R_4$ is phenyl substituted with one, two, or three groups selected from lower alkyl, lower alkoxy, hydroxy, trifluoromethyl, halo, and nitro.

7. A method of claim 6 employing a compound selected from:
8-Methoxy-3-(4-methyl-benzyl)-1,2,3,4-tetrahydro-chromeno[3,4-c]pyridin-5-one;
3-(3,4-Dichloro-benzyl)-8-methoxy-1,2,3,4-tetrahydro-chromeno[3,4-c]pyridin-5-one;
8-Methoxy-3-(4-nitro-benzyl)-1,2,3,4-tetrahydro-chromeno[3,4-c]pyridin-5-one;
3-(4-Chloro-benzyl)-8-methoxy-1,2,3,4-tetrahydro-chromeno[3,4-c]pyridin-5-one;
8-Methoxy-3-(3,4,5-trimethoxy-benzyl)-1,2,3,4-tetrahydro-chromeno[3,4-c]pyridin-5-one;
8-Methoxy-3-(4-trifluoromethyl-benzyl)-1,2,3,4-tetrahydro-chromeno[3,4-c]pyridin-5-one;
8-Methoxy-3-(4-methoxy-benzyl)-1,2,3,4-tetrahydro-chromeno[3,4-c]pyridin-5-one;
3-(3-Chloro-benzyl)-8-methoxy-1,2,3,4-tetrahydro-chromeno[3,4-c]pyridin-5-one;
3-(2-Chloro-benzyl)-8-methoxy-1,2,3,4-tetrahydro-chromeno[3,4-c]pyridin-5-one;
3-(4-Chloro-benzyl)-8-methyl-1,2,3,4-tetrahydro-chromeno[3,4-c]pyridin-5-one;
3-(4-Chloro-benzyl)-8,9-dimethoxy-1,2,3,4-tetrahydro-chromeno[3,4-c]pyridin-5-one; and
3-Benzyl-7,8-dimethoxy-1,2,3,4-tetrahydro-chromeno[3,4-c]pyridin-5-one.

8. A method of claim 1 employing a compound wherein n is 2, and $R_4$ is phenyl.

9. A method of claim 8 employing 8-Methoxy-3-phenethyl-1,2,3,4-tetrahydro-chromeno[3,4-c]-pyridin-5-one or 8,9-dimethoxy-3-phenethyl-1,2,3,4-tetrahydro-chromeno[3,4-c]pyridin-5-one.

10. A method of claim 1 employing a compound wherein n is 1, and $R_4$ is pyridyl.

11. A method of claim 10 employing a compound selected from:
8-Methoxy-3-pyridin-4-ylmethyl-1,2,3,4-tetrahydro-chromeno[3,4-c]pyridin-5-one;
8-Methoxy-3-pyridin-3-ylmethyl-1,2,3,4-tetrahydro-chromeno[3,4-c]pyridin-5-one; and
8-Methoxy-3-pyridin-2-ylmethyl-1,2,3,4-tetrahydro-chromeno[3,4-c]pyridin-5-one.

12. A method of claim 1 employing a compound wherein n is 1, and $R_4$ is quinolinyl.

13. A method of claim 12 employing 8-Methoxy-3-quinolin-4-ylmethyl-1,2,3,4-tetrahydro-chromeno[3,4-c]pyridin-5-one.

14. A method of claim 1 wherein the psychosis treated is schizophrenia.

15. A compound selected from:
3-Benzyl-8-methoxy-1,2,3,4-tetrahydro-chromeno[3,4-c]pyridin-5-one;
8-Methoxy-3-(4-methyl-benzyl)-1,2,3,4-tetrahydro-chromeno[3,4-c]pyridin-5-one;
3-(3,4-Dichloro-benzyl)-8-methoxy-1,2,3,4-tetrahydro-chromeno[3,4-c]pyridin-5-one;
8-Methoxy-3-(4-nitro-benzyl)-1,2,3,4-tetrahydro-chromeno[3,4-c]pyridin-5-one;
3-Benzyl-8,10-dihydroxy-9-methyl-1,2,3,4-tetrahydro-chromeno[3,4-c]pyridin-5-one hydrochloride;
3-(4-Chloro-benzyl)-8-methoxy-1,2,3,4-tetrahydro-chromeno[3,4-c]pyridin-5-one;
8-Methoxy-3-pyridin-4-ylmethyl-1,2,3,4-tetrahydro-chromeno[3,4-c]pyridin-5-one;
8-Methoxy-3-quinolin-4-ylmethyl-1,2,3,4-tetrahydro-chromeno[3,4-c]pyridin-5-one;
8-Methoxy-3-(3,4,5-trimethoxy-benzyl)-1,2,3,4-tetrahydro-chromeno[3,4-c]pyridin-5-one;
8-Methoxy-3-(4-trifluoromethyl-benzyl)-1,2,3,4-tetrahydro-chromeno[3,4-c]pyridin-5-one;
8-Methoxy-3-(4-methoxy-benzyl)-1,2,3,4-tetrahydro-chromeno[3,4-c]pyridin-5-one;
3-(3-Chloro-benzyl)-8-methoxy-1,2,3,4-tetrahydro-chromeno[3,4-c]pyridin-5-one;

3-(2-Chloro-benzyl)-8-methoxy-1,2,3,4-tetrahydro-chromeno[3,4-c]pyridin-5-one;

3-Benzyl-8-methyl-1,2,3,4-tetrahydro-chromeno[3,4-c]pyridin-5-one;

8-Methoxy-3-pyridin-3-ylmethyl-1,2,3,4-tetrahydro-chromeno[3,4-c]pyridin-5-one;

8-Methoxy-3-pyridin-2-ylmethyl-1,2,3,4-tetrahydro-chromeno[3,4-c]pyridin-5-one;

3-(4-Chloro-benzyl)-8-methyl-1,2,3,4-tetrahydro-chromeno[3,4-c]pyridin-5-one;

3-(4-Chloro-benzyl)-8,9-dimethoxy-1,2,3,4-tetrahydro-chromeno[3,4-c]pyridin-5-one;

8-Methoxy-3-phenethyl-1,2,3,4-tetrahydro-chromeno[3,4-c]pyridin-5-one; and 8,9-Dimethoxy-3-phenethyl-1,2,3,4-tetrahydro-chromeno[3,4-c]pyridin-5-one hydrochloride.

16. A pharmaceutical composition comprising a compound of claim 15 together with a pharmaceutically acceptable diluent, carrier, or excipient therefor.

* * * * *